USOO5939325A

United States Patent [19]
Speck et al.

[11] Patent Number: 5,939,325
[45] Date of Patent: Aug. 17, 1999

[54] STABLE WHOLE BLOOD COAGULATION CONTROLS

[75] Inventors: Roy E. Speck, Indianapolis; Ruby P. Bonderman, Fishers, both of Ind.

[73] Assignee: Analytical Control Systems, Inc., Fishers, Ind.

[21] Appl. No.: 08/458,630

[22] Filed: Jun. 2, 1995

Related U.S. Application Data

[63] Continuation of application No. 08/112,154, Aug. 26, 1993, abandoned, which is a continuation-in-part of application No. 08/004,188, Jan. 13, 1993, abandoned, which is a continuation of application No. 07/754,166, Sep. 3, 1991, abandoned, which is a continuation of application No. 07/383,004, Jul. 20, 1989, abandoned.

[51] Int. Cl.$^6$ ........................... G01N 31/00; G01N 33/86
[52] U.S. Cl. .................................. 436/16; 436/8; 436/18; 436/69; 435/13
[58] Field of Search ..................................... 436/8–18, 69; 424/3; 252/408.1; 435/13

[56] References Cited

U.S. PATENT DOCUMENTS

| | | | |
|---|---|---|---|
| 4,056,484 | 11/1977 | Heimburger et al. | 436/16 |
| 4,234,682 | 11/1980 | Bartl et al. | 435/13 |
| 4,271,122 | 6/1981 | Strassle et al. | 436/16 |
| 4,301,028 | 11/1981 | Bartl et al. | 436/8 |
| 4,382,028 | 5/1983 | Paget | 530/364 |
| 4,409,334 | 10/1983 | Lill et al. | 436/8 |
| 4,624,927 | 11/1986 | Fukushima et al. | 436/16 |
| 4,632,907 | 12/1986 | Sato et al. | 436/10 |
| 4,731,330 | 3/1988 | Hill et al. | 436/16 |
| 4,877,741 | 10/1989 | Babcock et al. | 436/8 |

FOREIGN PATENT DOCUMENTS

WO 91/01497  2/1991  WIPO.

OTHER PUBLICATIONS

Saunders Dictionary & Encyclopedia of Laboratory Medicine and Technology, p. 1605, W.B. Saunders Company, Oct. 1988.

M. Brozovic et al., "Stability of Freeze–Dried Plasma Prepared from Patients on Oral Anticoagulants", *Journal of Clinical Pathology*, 26, 1973, pp. 857–863.

R. Radcliffe and Y. Nemerson, "Bovine Factor VII", *Methods in Enzymology*, XLV (B), 1976, pp. 49–56.

T. Koide et al., "Bovine Factor XI (Plasma Thromboplastin Antecedent", *Methods in Enzymology*, XLV (B), 1976, pp. 65–73.

K. Fujikawa and E. W. Davie, "Bovine Factor IX (Christmas Factor)", *Methods in Enzymology*, XLV (B), 1976, pp. 74–83.

M. E. Legaz and E. W. Davie, "Bovine Factor VIII (Antihemophilic Factor)", *Methods in Enzymology*, XLV (B), 1976, pp. 83–89.

K. Fujikawa and E. W. Davie, "Bovine Factor X (Stuart Factor)", *Methods in Enzymology*, XLV (B), 1976, pp. 89–95.

J. Jesty and Y. Nemerson, "The Activation of Bovine Coagulation Factor X", *Methods in Enzymology*, XLV (B), 1976, pp. 95–107.

R. W. Colman and R. M. Weinberg, "Factor V", *Methods in Enzymology*, XLV (B), 1976, pp. 107–122.

K. G. Mann, "Prothrombin", *Methods in Enzymology*, XLV (B), 1976, pp. 123–156.

K. D. Miller, "Horse Prothrombin", *Methods in Enzymology*, XIX, 1970, pp. 140–145.

S. Magnusson, "Bovine Prothrombin and Thrombin", *Methods in Enzymology*, XIX, 1970, pp. 157–184.

K. Fujikawa et al., "Bovine Factors $X_1$ and $X_2$ (Stuart Factor). Isolation and Characterization", *Biochemistry*, 11(26), 1972, pp. 4882–4891.

R. J. Dupe and R. M. Howell, "The Purification and Properties of Factor X from Pig Serum and its Role in Hypercoagulability in vivo", *Biochemical Journal*, 133, 1973, pp. 311–321.

G. Contant et al., "Heparin Inactivation During Blood Storage: Its Prevention by Blood Collection in Citric Acid, Theophylline, Adenosine, Dipyridamole", *Thrombosis Research*, 31, 1983, pp. 365–374.

Hemotec, Inc., 7103 S. Revere Parkway, Englewood, CO 80112–3992, Product Bulletin describing CLOTtrac™ HR Control, date unknown.

Kendall McGaw Laboratories, Inc., Irvine, CA 92714–5895, Product Bulletin describing Monitoring Anticoagulation Using the ACTester™/ACTest™ AACT System, date unknown.

International Technidyne Corporation, 23 Nevsky Street, Edison, NJ 08820, Product Bulletin describing Hemochron® Coagulation Controls and Tests, date unknown.

J. Gajewski et al., "Blood Coagulation Value of Sheep", *American Journal of Veterinary Research*, 32(3), 1971, pp. 405–409.

C.E. Greene, et al., "Coagulation Studies of Plasmas from Health Domesticated Animals and Persons", *American Journal of Veterinary Research*, 42(12), 1981, pp. 2170–2177.

*Primary Examiner*—Maureen M. Wallenhorst
*Attorney, Agent, or Firm*—Kenyon & Kenyon

[57] ABSTRACT

Stable coagulation controls containing mammalian blood and at least one non-primate mammalian coagulation factor or non-primate mammalian blood are described. The whole blood coagulation controls have a clotting time in the range of normal human clotting times or abnormal human clotting times.

24 Claims, No Drawings

STABLE WHOLE BLOOD COAGULATION CONTROLS

This application is a continuation of application Ser. No. 08/112,154, filed on Aug. 26, 1993, now abandoned, which is a continuation-in-part of Ser. No. 08/004,188 filed on Jan. 13, 1993, now abandoned, which is a continuation of Ser. No. 07/754,166 filed on Sep. 3, 1991, now abandoned, which is a continuation of Ser. No. 07/383,004 filed on Jul. 20, 1989 now abandoned.

BACKGROUND OF THE INVENTION

The present invention relates generally to blood coagulation, and more particularly to improved blood coagulation controls which demonstrate superior stability, and also sensitivity to variation in reagents used in coagulation tests. The coagulation control technology described herein is particularly suited to monitoring procedures for whole blood coagulation determinations for patients.

The need for stable and reliable blood coagulation controls is well documented. The continued and increased use of oral anticoagulants for treatment and management of various thrombo-embolytic conditions today, more than ever, is a driving force for their development. As is known, overdosage of anticoagulants, commonly the coumarin derivatives, can lead to serious complications, including hemorrhage from peptic ulcers, as well as other gastrointestinal complications. On the other hand, maintenance of too low a level of anticoagulant reduces or eliminates the efficacy of the prescribed treatment.

It is therefore extremely important that anticoagulant levels be reliably monitored, and, as such, a voluminous body of art has developed documenting attempts of those in the field to produce stable and reliable controls, as well as reagents, to aid in monitoring anticoagulant activity.

For example, U.S. Pat. No. 3,947,378 to Babson discloses a process for producing a control plasma deficient in Factors II, VII, IX, and X which involves treating to plasma with 20 to 22% by weight of barium sulfate at ambient temperature and then removing the adsorbent from the adsorbed plasma. The Babson patent reports that abnormal control plasmas produced by mixing the so-adsorbed plasma with normal plasma are more stable after reconstitution and give more uniform results in the activated partial thromboplastin time (APTT) procedure after storage of up to eight hours or more.

S. Zucker, M. H. Cathey, and B. West, *Preparation of Quality Control Specimens for Coagulation*, Amer. J. Clin. Path., June 1970, Vol. 53, pp. 924–927, reports a method for preparing lyophilized plasma specimens for use as quality controls in coagulation testing. Zucker et al. report buffering the plasma specimens with N-2-hydroxyethylpiperazine-N'-2-ethanesulfonic acid (HEPES), which was reported to provide pH and enzyme stability for prothrombin times for eight hours at 25° C. An article by M. Brozovic, D. J. Howarth, L. P. van Halem Visser, and E. A. Loeliger, *Stability of Freeze-Dried Plasma Prepared from Patients on Oral Anticoagulants*, Journal of Clinical Pathology, 1973, Vol. 26, pp. 857–963, reported as to the suitability of freeze-dried plasmas from patients on oral anticoagulants to serve as reference material in the calibration of thromboplastins used in the control of oral anticoagulant treatment. The authors studied plasmas from several plasma pools, developed by collecting from each patient 4.5 ml of blood into 0.5 ml of a solution formed by combining 44.62 g of HEPES buffer, 38.00 g trisodium citrate ($2H_2O$), and 0.5 ml aprotinin TRASYLOL (1000 $\mu$/ml), and then adding distilled water to 1000 ml. Individual samples were centrifuged, as were the subsequently pooled samples, whereafter 1 ml of 10% sodium azide was added per liter of plasma. Samples of the prepared plasmas were then either frozen or freeze-dried. The authors reported that the freeze-dried plasmas from patients on oral anticoagulants could be used to calibrate thromboplastins provided that they are used immediately after complete reconstitution or kept at 4° C. for use within four to six hours of reconstitution. The authors also reported that their plasma samples generally demonstrated varying levels and types of instability after reconstitution and storage at 4° C., 22° C., and 37° C. It was generally reported that this instability resulted after about twenty-four hours at the lower two temperatures and after about four to six hours at the higher 37° C. temperature.

U.S. Pat. No. 4,007,008 to Becker et al. describes a method for reducing enzyme activities in animal serum or plasma including the steps of raising the pH thereof to a level about that of normal serum by adding a base, and thereafter terminating the reaction or reduction of enzyme activities neutralizing the serum or plasma with an acidic medium.

Other general background can be found in U.S. Pat. No. 3,799,885 to Dennis et al. which discloses a calcium chloride test reagent buffered with HEPES buffer which is especially adapted for use in monitoring heparin therapy; in U.S. Pat. No. 4,301,028 to Bartl et al. which reports a control reagent for heparin activity determination; in U.S. Pat. No. 4,116,336 to Sorenson et al. which relates to a package containing a synthetic reference liquid for quality control and/or calibration of blood gas measuring equipment; and in P. S. Roberts, H. N. Hughes, and P. B. Fleming, *The Effects of Hepes Buffer on Clotting Tests, Assay of Factors V and VIII* and on the *Hydrolysis of Esters by Thrombin and Thrombokinase*, Thrombos, Haemostas, (Stuttg.), 1976, Vol. 35, p. 202, wherein the authors report faster clotting in the presence of 50 mM HEPES buffer.

Another aspect of the prior art control plasmas is that a majority of them, especially those commercially available, consist of or otherwise comprise primate plasma, most commonly human. These plasmas present disadvantages in that they contain unstable human factors, particularly Factors V and VIII, and also present a greater risk to the preparer or user of the controls, since they may harbor active AIDS or hepatitis viruses.

In the face of the voluminous literature and other work relating to plasmas for coagulation controls, there still remains a need for a coagulation control which exhibits superior stability with respect to one-stage prothrombin times (PT), activated partial thromboplastin times (APTT), and Factor V and VIII activity values, as well as superior sensitivity to variations in clotting test reagents employed. Certain forms of improved controls would also significantly eliminate risk of AIDS or hepatitis contraction to those who prepare and use it. For example, a coagulation product described as the CLOTrac™ HR control appears to be stable only for 2 hours at room temperature following reconstitution.

The applicant's invention, in its various aspects, addresses these matters.

SUMMARY OF THE PREVIOUS DEVELOPMENT

Accordingly, one preferred embodiment of the applicant's invention relates to a stable coagulation control plasma comprising blood plasma, and effective amounts of (a) a buffer to maintain a physiological pH, (b) a protease inhibitor, and (c) a suitable stabilizing carbohydrate. In a preferred aspect the control has a total plasma component constituted substantially of non-primate plasma.

Another preferred embodiment of the applicant's invention relates to a coagulation control plasma having high stabilized levels of Factor V and VIII. This control comprises plasma and at least about 2 weight percent of a suitable carbohydrate. The plasma of this embodiment is derived from blood which has been collected directly from an animal source into a solution containing a buffer to maintain a physiological pH, a protease inhibitor, and citrate. The carbohydrate in the control is added after removal of red blood cells from the blood.

Another preferred embodiment of the applicant's invention relates to a process for producing a stable coagulation control plasma. This process includes the sequential steps of collecting the blood from which the plasma is derived directly from an animal source into a solution containing a buffer to maintain physiological pH, a protease inhibitor, and citrate; removing red blood cells from said blood; and adding a suitable stabilizing carbohydrate.

Still another preferred embodiment of this invention relates to a process for producing a stable coagulation control which includes the steps of providing blood plasma; and, adding to said blood plasma at least one purified, stabilized coagulation factor.

SUMMARY OF THE PRESENT INVENTION

According to the practice of the present invention there is provided a coagulation control effective to confirm the reproducibility of a procedure monitoring coagulation capability in a human patient wherein said procedure provides a predetermined clotting time for said patient, said control comprising an amount of primate blood plasma, or an extract thereof, containing one or more labile coagulation factors having predetermined activities, said control further comprising an amount of one or more non-primate mammalian coagulation factors corresponding to said one or more labile factors, wherein said control is capable of confirming, if maintained, in liquid form, for at least about 3 days at room temperature or at least about 8 hours at 37° C., that the clotting time for said procedure does not change by more than about 10% from said predetermined value thereof, said one or more non-primate factors being present in said control in amounts sufficient to replace therein any activity corresponding to said one or more labile factors lost during said period of maintenance.

The clinical controls provided according to the practice of the invention are particularly stable with respect to the activities of factors II, V and VIII contained therein.

In representative embodiments of the invention, there are provided coagulation controls comprising a volume of primate blood plasma, or an extract therefrom, and further comprising a volume of plasma from a non-primate equal to at least about a 1/100 fraction of said volume of primate plasma wherein the activity of factor II, V or VIII provided by said volume of non-primate plasma is equal to at least about 70% of the activity of one or more of said corresponding factors as provided therein by said primate plasma.

Additionally, there is provided a coagulation control effective to confirm the reproducibility of a procedure monitoring coagulation capability in a human patient wherein said procedure provides a predetermined clotting time for said patient, said control comprising an amount of primate blood plasma, or an extract thereof, containing one or more labile coagulation factors having predetermined activities, said control further comprising an amount of one or more non-primate mammalian coagulation factors corresponding to said one or more labile factors, wherein said control is capable of confirming, if maintained in liquid form, following lyophilization and reconstitution therefrom, for at least about 3 days at room temperature or at least about 8 hours at 37° C., that the clotting time for said procedure does not change by more than about 10% from said predetermined value thereof, said one or more non-primate factors being present in said control in amounts sufficient to replace therein any activity corresponding to said one or more labile factors lost during said period of maintenance.

A still further embodiment of the present invention provides for a coagulation control effective to confirm the reproducibility of a procedure monitoring coagulation capability in a human patient wherein said procedure provides a predetermined clotting time for said patient, said control comprising an amount of primate blood plasma, or an extract thereof containing one or more labile coagulation factors having predetermined activities, said control further comprising an amount of one or more non-primate mammalian coagulation factors corresponding to said one or more labile factors, wherein said control is capable of confirming, after being maintained for at least about 2 years in a lyophilized state at about 2 to about 8° C., and then reconstituted therefrom, that the clotting time for said procedure does not change by more than about 10% from said predetermined value thereof, said one or more non-primate factors being present in said control in amounts sufficient to replace therein any activity corresponding to said one or more labile factors lost during said period of maintenance in the lyophilized state. Stabilities in lyophilized form at 2 to 8° C. of up to 5 or more years are also provided.

DESCRIPTION OF PREFERRED EMBODIMENTS OF THE INVENTIONS

One preferred embodiment of the applicant's invention relates to a stable coagulation control plasma which comprises blood plasma, and effective amounts of (a) a buffer to maintain a physiological pH, (b) a protease inhibitor, and (c) a suitable stabilizing carbohydrate. It is contemplated that a carbohydrate as used herein would have ratios of H to O of 2 to 1, as is understood in that art.

As to types of plasmas which are suitable for this embodiment, primate and non-primate plasmas can be used. Preferred plasmas to date have been human, bovine, porcine, equine and rabbit plasmas, although other plasmas including, for instance, goat and sheep plasmas, can be used. Additionally, in this embodiment of the invention, these plasmas may be collected in any suitable manner as known in the art.

As to the composition of the blood plasma in the control, various animal plasmas may be used individually or combined, adsorbed or non-adsorbed. In most cases, however, the applicant has to date preferred combining the plasmas of two or more types of animal. Since different animals have differing levels and differing stabilities of their respective coagulation factors, different animal plasmas can be selected and combined to adjust the ratios of coagulation factors in the controls and thus also adjust stability of the control and clotting times of the PT, APTT, and other tests.

For instance, owing to their particular coagulation constituent levels, rabbit plasma is used to shorten PT values, porcine plasma is used to shorten APTT but not PT values, bovine plasma is used to furnish high levels of factor V, and equine plasma is used to prolong the APTT but not the PT value. By using these principles, the applicant has been able to prepare, as desired, control plasmas exhibiting particular ranges (e.g., normal or abnormal) of PT and APTT values. Clotting times can thus be precisely adjusted according to the types and ratios of plasmas used.

Of the preferred control plasmas which have been prepared to date, four have shown to be more preferred. The first exhibits PT and APTT values in the normal range, and has a total plasma component constituted of porcine, bovine and rabbit plasma in ratios of about 1:6:3, respectively. The second has PT and APTT values in the abnormal range and has a total plasma component constituted of porcine plasma adsorbed with aluminum hydroxide gel, and bovine plasma in a ratio of about 35:1, respectively. The third plasma also exhibits PT and APTT times in the abnormal range, and has a total plasma component constituted of porcine plasma adsorbed with aluminum hydroxide gel.

These first three more preferred plasmas provide the advantage of significantly reduced risk of HIV or hepatitis virus infection by those who prepare and/or use them since the pertinent viruses are not present in the non-primate plasmas. Additional advantages have related to high and stable levels of coagulation factors these plasmas have provided. In this regard, it is understood that similar advantages can be derived so long as the non-primate plasma constitutes at least a substantial part of the total plasma component of the control, and thus such control plasmas are also a preferred aspect of this invention, as are controls whose plasma component consists essentially of non-primate plasmas.

The fourth more preferred control has a plasma component constituted of normal human, bovine, and rabbit plasma in respective ratios of about 2:2:1.

With respect to the buffer, to date, HEPES buffer has been preferred, although many other buffers, for instance TRIS, are known and are suitable. The preferred HEPES buffer has been HEPES hemi sodium, which is preferably present in the control in an amount of at least about 0.08 M, and preferably above 0.05 in amount.

As to amounts and types of protease inhibitor and carbohydrate, it has been preferred to date that the inhibitor and carbohydrate be present in the control in amounts of at least about 0.5 U/ml, and 2 weight percent, respectively. The preferred protease inhibitor has been aprotinin, although other such protease inhibitors, for instance soya bean trypsin inhibitors, are known in the art and are suitable. The preferred stabilizing carbohydrate to date has been saccharides, and in particular, sucrose, although others well known in the art can also be used. Additionally, it has been more preferred to date that the sucrose be present in the control in an amount of about 5 weight percent.

As to other components of the control plasma of this preferred embodiment, it has also been preferred that the control plasma include thimerosal in an amount of preferably at least about 0.02 weight percent and/or sodium azide in an amount of preferably at least about 0.08 weight percent.

To formulate a batch of control plasma, approximately 1 part (by volume) of the applicant's preferred buffering and preservative solution described in Example 1 below are combined with about 9 parts plasma. More preferred to date has been to combine approximately 1 part of the applicant's preferred buffering preservation solution with about 9 parts of mixed or unmixed non-primate animal plasma.

Further details of the preparation of the control plasmas of this preferred embodiment, as well as details of their stability, can be found in Examples 1–6 and Tables 1–3 below. Collectively, the control plasmas of this embodiment have generally proven stable, meaning that APTT and PT analyses do not change more than about 10% for at least about 3 days at room temperature, or at least about 8 hours at 37° C.

Additionally, as is particularly detailed in Example 6 below, the coagulation controls of this preferred embodiment have demonstrated increased sensitivity to variations in reagents used in clotting time testing. Example 6 details experiments wherein a coagulation control sample prepared in accordance with this embodiment was tested against a commercially available plasma, CITROL I, and fresh normal human plasma as regards sensitivity to dilutions of thromboplastin reagent in the PT test. As the reported results demonstrate, the control prepared in accordance with the applicant's invention herein demonstrated superior sensitivity to the varying dilutions of thromboplastins.

As stated, another preferred embodiment of the present invention involves a coagulation control plasma having high stabilized levels of Factor V and VIII. This control comprises plasma derived from blood which has been collected directly from an animal source into a collecting solution containing a buffer to maintain physiological pH, a protease inhibitor, and citrate, and to which, after removal of red blood cells, has been added at least about 2 weight percent of a suitable stabilizing carbohydrate.

Although others can be used, to date, the preferred buffer into which the blood has been collected has been HEPES hemi-sodium, and the preferred protease inhibitor has been aprotinin. It has also been preferred that the HEPES hemi-sodium and the aprotinin be present in the collecting solution in respective amounts of at least about 0.25 M and 5 U/ml. Citrate can be present in the collecting solution in suitable amount as known in the art. To date, however, it has been preferred that sodium citrate be present in an amount of about 3 weight percent. When these preferred amounts of HEPES hemi-sodium, aprotinin, and citrate are used, about 9 parts (by volume) blood are preferably collected into about 1 part of the collection solution.

The carbohydrate can be added in solid form or in solution. Again, the preferred carbohydrate has been sucrose, which has been added after removal of red blood cells from the plasma by centrifuging or another suitable method. Additionally, it has been more preferred to add sucrose to a level of about 5 weight percent in the control. If desired, additional physiological pH buffer can also be added (as a solid or in solution) to effect a desired level in the final control. Preferably, the final control has also contained thimerosal (preferably at least about 0.02 weight percent) and sodium azide (preferably at least about 0.08 weight percent). The thimerosal and/or sodium azide can be present initially in the collecting solution or can be added later as a solid or in solution.

The applicant has discovered that preferred plasmas prepared according to this embodiment are very high in Factor V and VIII content. Additionally, the applicant has found that the Factor V and VIII contents thus produced are highly stable at both room temperature (for at least about 3 days) and at about 37° C. (for at least about 8 hours).

Plasmas which are suitable for this embodiment of the invention include primate and non-primate plasmas, with preferred plasmas being beef, pig, rabbit, horse, and human plasmas. Additional details of the preparation of control plasmas of this embodiment can be found in Examples 7–11 below.

Another preferred embodiment of the present invention concerns a method for producing a stable coagulation control. As stated above, this method includes the sequential steps of (a) collecting the blood containing the plasma to be used in the control directly from an animal source into a solution containing a buffer effective to maintain a physiological pH, a protease inhibitor, and citrate, (b) removing red blood cells from said blood, and (c) adding at least about 2 weight percent of a suitable stabilizing carbohydrate. Further details of this preferred process are analogous to those discussed in the embodiment immediately above, and can further be found in Examples 7–11 below.

Still another preferred embodiment of this invention concerns a method for producing a stable coagulation control plasma, which method involves the steps of providing blood plasma, and adding to said plasma at least one stable purified coagulation factor in order to increase the level of the added factor in the plasma. As is further detailed in Example 12 below, particular factors are purified from various animal plasmas as known in the art. These purified factors are then added to plasma to increase the level of the added factor in the plasma and to adjust the PT and/or APTT values. Preferred methods also involve adding to equine or human plasma stable purified Factor V or VIII from bovines or porcines. Additionally, purified equine Factor II has proven particularly stable and can be added to other plasmas as a source of stable Factor II. Collectively, the plasmas to which the stable purified factors have been added have demonstrated stability superior to similar plasmas without the added factors.

Reference will now be made to specific Examples and Tables for the purposes of further describing and understanding the features of the applicant's preferred embodiments as well as their advantages and improvements over the art. It should be understood that these Examples are representative only, and that such additional embodiments and improvements of the same are within the contemplation and scope of the applicant's invention as would occur to one of ordinary skill in this art.

The Factor V and VIII activity values reported in the following Examples were calculated in the conventional manner against a standard curve prepared from dilutions of normal human plasma. PT intends the one-stage prothrombin time, and APTT intends the activated partial thromboplastin time. The PT and APTT tests reported were performed in the conventional manner.

DESCRIPTION OF PREFERRED EMBODIMENTS OF THE PRESENT INVENTION

Coagulation controls, including whole blood coagulation controls that comprise a volume of primate blood plasma, or an extract therefrom, and further comprise a volume of non-primate plasma, or an extract therefrom, wherein the activities of one or more of factors II, V or VIII contained therein are stable for a period of at least about 3 days at room temperature or at least about 8 hours at 37° C. when the control is in liquid form. Additionally, with respect to certain controls, the activities of factors II, V and VIII are stable in a period of storage under lyophilized conditions of 2 or more years, and 2typically of 5 or more years.

Equivalent controls are provided according to the practice of the invention wherein no primate plasma is present and plasmas, or extracts therefrom, from appropriate source mammals are used to provide stable factors.

As aforementioned, a characteristic difficulty with prior art clotting (coagulation) controls is that, owing to loss of activity of labile factors, they are only of limited utility in the monitoring of coagulation (clotting) capability in a patient. Most particularly factors V and VIII are subject to loss of activity.

One aspect of improving stability of such controls according to the practice of the invention concerns direct collecting of a plasma for a control into a preferred collecting solution (see Examples 7 to 11). In this regard aprotinin is a most preferred protease inhibitor.

In accord with the practice of the invention, activities of factor V, VIII and also II are stabilized by using non-primate source animals for which such factors are very stable and/or present in high concentration, the identity of such mammals being capable of determination according to the art.

For the purposes of the present invention the "activity" associated with an amount of coagulation factor is defined as maintained, whether by replacement or supplementing of that factor from another mammal, when the performance of a coagulation procedure (providing a clotting time) is substantially unaffected (typically not lengthened by more than 10%), for example, owing to the beneficial presence of said replacement or supplementing factor. As is recognized in the art, controls may contain plasma or extracts (fractions) of plasma, all such substances being useful in the practice of the invention if all coagulation factors needed in the control come to be provided.

Controls useful in the practice of the invention provide the aforementioned labile factors (and factor activities) and may be formulated with plasma or plasma extract of any other mammal whether primate or non-primate.

As described according to Example 13 below, such controls are particularly useful as whole blood clotting controls using testing methodology known in the art for such purposes.

Typically according to the practice of the invention, a coagulation control is formulated using an amount of plasma or plasma extract to provide an activity of factor II, V or VIII (or combinations thereof) that is equal to at least about 50%, and preferably at least about 70%, of the activity of said one or more factors as provided therein from other source mammals. Alternatively plasma of only those species providing non-labile factors II, V and VIII may be used.

Normally the ratio of plasma volume (or of plasma extract equivalent) of each mammal providing said one or more non-labile factors (II, V or VII) to that of the other provided mammal volume (or of extract therefor) is at least 1 to 10,000, preferably 1 to 5000, more preferably 1 to 1000 or up to about 1 to 100, or 1 to 50 or higher.

Particularly preferred examples are swine plasma (for factor VIII) at 1 to 1000, bovine plasma (for factor V) at 1 to 100, and horse plasma (for factor II) at 1 to 1000. Further representative examples are defined according to the claims as provided below.

An additional advantage of the invention (see Example 15) is represented by lyophilized controls that have substantial stability when stored in lyophilized form (see Example 15) and that after reconstitution to liquid form are stable for more than 1 day at room temperature preferably more than 2 days at room temperature, and typically more than 3 days at room temperature or at least about 8 hours at 37° C.

EXAMPLE 1

Preparation of Preferred Preservation Solution 100 ml of the applicant's preferred preservative solution were prepared by mixing 500 U aprotinin, about 12.5 g HEPES hemi sodium, 0.1 g thimerosal, 0.5g NaN₃, and 25 g sucrose, and then adding distilled water to 100 ml. This preparation resulted in 100 ml of preservative solution which consisted of:

(a) 0.5 M HEPES hemi sodium;
(b) 0.1% thimerosal;
(c) 25% sucrose;
(d) 0.5% sodium azide; and
(e) 500 U aprotinin.

EXAMPLE 2

Non-Primate Based Normal Range Control (Level 1)

A pilot lot (hereafter designated P1) of non-primate based control was prepared which demonstrated PT and APTT values in the normal range. Particularly, 54 ml beef plasma, 9 ml pig plasma, and 27 ml rabbit plasma were blended with 10 ml of the preferred preservative solution of Example 1. The initial PT and APTT values were 11.0 and 24.1 seconds, respectively. The lot was divided out into 1.0 ml portions which were placed into individual vials and lyophilized in a conventional manner. A vial of the P1 control plasma was reconstituted the next day with distilled water, whereafter it demonstrated a PT value of 11.0 seconds and an APTT value of 24.1 seconds. Similarly reconstituted P1 vials were allowed to stand at room temperature (about 25° C.) for up to five days, one being tested each day for PT and APTT values. The results are given in TABLE 1 below, and demonstrate excellent stability.

TABLE 1

| Day | 2 | 3 | 4 | 5 |
|---|---|---|---|---|
| PT | 11.2 | 10.8 | 11.7 | 11.2 |
| APTT | 25.7 | 26.2 | 27.1 | 28.3 |

Equally surprising stabilities for Factors V and VIII were shown in the P1 samples. Immediately after reconstitution, P1 samples exhibited Factor V and VIII values of approximately 1000% and 110%, respectively, of the amounts found in normal human plasma pools. After reconstituted samples were allowed to stand for five days at room temperature, they demonstrated a Factor V value of approximately 1100% and a Factor VIII value of approximately 90%.

EXAMPLE 3

Non-Primate Based Normal Range Control (Level 2)

A second pilot lot (P2) of control plasma was prepared by combining 175 ml adsorbed pig plasma, 5 ml beef plasma, and 20 ml of the applicant's preferred preservative solution prepared as in Example 1 above. This lot was prepared so as to have abnormal clotting times, with initial PT and APTT values being 21.1 and 40.8, respectively. The P2 lot was divided and lyophilized in the same manner as the P1 lot described in Example 2 above. After reconstitution with distilled water, a vial of the P2 lot produced a PT value of 20.1 and a APTT value of 41.4 seconds.

Analogous to the reconstituted stability tests of Example 2, several reconstituted P2 vials were allowed to stand at room temperature for up to five days with one being tested each day for PT and APTT values. TABLE 2 below sets forth the results which again demonstrate superior stability.

TABLE 2

| Day | 2 | 3 | 4 | 5 |
|---|---|---|---|---|
| PT | 20.6 | 22.0 | 21.6 | 22.7 |
| APTT | 43.8 | 46.1 | 44.1 | 44.4 |

EXAMPLE 4

Non-Primate Based Abnormal Range Control (Level 3)

A third pilot lot (P3) of control plasma was prepared by combining 90 ml adsorbed (with aluminum hydroxide gel) pig plasma with 10 ml of the applicant's preferred preservative solution prepared in accordance with Example 1 above. Initial PT and APTT values of 41.3 and 69.9 were observed for this P3 material. The P3 material was then divided and lyophilized as were the P1 and P2 lot materials of Examples 2 and 3 above. After reconstitution and storage at room temperature for about one day, a vial of P3 material was analyzed. The PT and APTT values for this reconstituted P3 plasma were 38.1 and 64.1, respectively, showing good stability.

EXAMPLE 5

Human/Non-Primate Normal Range Control 36 ml normal human plasma and 36 ml bovine plasma were combined with 18 ml rabbit plasma and 10 ml of the preservative solution of Example 1 to form a fourth pilot lot (P4) of control material. Initial PT and APTT values were in the normal range at 11.4 and 25.7, respectively. This P4 plasma also demonstrated good stability. A reconstituted sample allowed to stand at room temperature for 7 days registered a PT value of 11.5 and an APTT value of 29.7.

EXAMPLE 6

Sensitivity to Reagent Variations

In this Example, the sensitivity of the applicant's preferred control plasmas to variations in clotting time reagents was compared to that of fresh, normal plasma, and to that of CITROL I, a commercially available control plasma marketed by American Dade. The PT test was used in this determination. To perform the study, reagents consisting of 100, 80, 60, 40, 20 and 10% thromboplastin were prepared by diluting the thromboplastin using 0.025 M HEPES buffer, pH 7.35 containing 0.154 M sodium chloride. These reagent dilutions were then used to evaluate the PT values for the three test plasmas. The results are given in TABLE 3 below. As can be seen, the applicant's P1 control plasma material demonstrated significantly greater variation in PT values resulting from a greater sensitivity to the thromboplastin dilutions. Thus this increase in sensitivity allows detection of defective reagents more readily than even flesh plasma.

TABLE 3

| % Thromboplastin | PT/Fresh Normal Plasma | PT/ CITROL I | PT/ P1 Plasma |
|---|---|---|---|
| 100 | 11.5 | 11.4 | 11.3 |
| 80 | 11.6 | 11.8 | 12.1 |
| 60 | 12.4 | 12.7 | 13.3 |
| 40 | 13.5 | 13.7 | 14.9 |

TABLE 3-continued

| % Thromboplastin | PT/Fresh Normal Plasma | PT/ CITROL I | PT/ P1 Plasma |
|---|---|---|---|
| 20 | 15.9 | 16.4 | 18.3 |
| 10 | 18.8 | 19.5 | 22.6 |

EXAMPLE 7

Preferred Collecting Solution 100 ml of the applicant's preferred collecting solution were prepared by mixing 500 U aprotinin, about 6.25 g HEPES hemi sodium and 2.94 g sodium citrate, and adding distilled water to 100 ml. This preparation resulted in 100 ml of collecting solution which contained:

(a) 0.25 M HEPES hemi sodium;
(b) 2.94 gm sodium citrate; and
(c) 500 U aprotinin.

Preferably, about 9 parts by volume of blood has been collected into about 1 part by volume of this preferred collecting solution.

EXAMPLES 8–11

Direct Collection into Collecting Solution

In order to obtain a control plasma which has high and stable levels of coagulation Factors, particularly Factors V and VIII, Examples 2–6 are repeated except the plasma used is derived from blood which has been collected directly from the animal source into the applicant's preferred collecting solution of Example 7, and, after removal of red blood cells, sucrose, additional HEPES hemi sodium, as well as thiomersal and sodium azide are added in amounts to achieve the same respective levels as in Examples 2–6. The initial Factor V and VIII activity values are tested and are found to be particularly high as compared to plasmas which are collected into simple conventional citrated anticoagulant solutions. Additionally, the Factor V and VIII values are stabilized by the buffering and preservative solution, as is borne out by high Factor V and VIII values obtained after lyophilization and reconstitution, and after reconstituted control plasma samples are allowed to stand at 37° C. for eight hours, and at room temperature for about 3 days. PT and APTT values are similarly stable upon testing after reconstituted control plasmas are subjected to these temperature/time conditions.

EXAMPLE 12

Adding Stable Purified Factors

Pooled normal human plasma was assayed and demonstrated respective APTT and PT values of 34 secs and 13 secs. In various experiments, purified factors V and VIII from pig, cow, horse, sheep or rabbit were added to about 1 ml samples of the normal human plasma and in each instance corrected APTT to 26 secs. Similarly, purified Factor II from pig, cow, horse, sheep, or rabbit was added to about 1 ml samples of the normal human plasma and corrected PT to 11 secs. Additionally, in each instance, the lyophilized product showed better stability than the lyophilized normal human plasma.

EXAMPLE 13

Preparation of a Whole Blood Control Entirely from Non-Primate Plasma

A 1 liter volume of whole sheep blood was frozen, thawed, and then centrifuged at approximately 50,000 rpm in a flow through rotor of a Sharpies centrifuge (at about 50 ml/min) to remove cell membrane debris such as stroma (red blood cell ghosts) and most of the platelet membrane ghosts. A residual amount of platelet membrane material (providing, for example, Platelet factor 3) remains in the supernatant along with clotting factors and the hemoglobin. To 1 liter volume of supernatant was added a 200 ml volume of a normal animal control plasma, itself comprising a 1:1:1 (v/v/v) mixture of pig, cow, and horse plasmas to increase and to stabilize, the activity of, for example, factor II, V and VIII.

Antifoam C (product No. A-8011 Sigma Chemical Company), itself a silicon-based surfactant, is added from a 30% stock solution to a 0.1% to 0.3% final concentration and the resultant mixture is made also 8% (w/v) in sucrose. Without being limited as to theory, the antifoam C is believed to act as a surfactant increasing surface tension, and wetting of the control thereby facilitating reconstitution from the lyophilized state and minimizing foaming. Similarly, and without limitation as to theory, sucrose is representative of many substances known in the art that act as binders and facilitate protection of the proteins of the control during drying. Lyophilization was then conducted to constant dryness (i.e., no more than 3% pellet dryness and under typical conditions as used in the art) with reconstitution being accomplished with a volume of water equivalent to the original dispensed sample following by mixing with an equal volume of 200 mM $CaCl_2$ solution. Using diatomaceous earth as an activator, the above formula gave from 90 to 120 seconds control clotting time in a procedure using appropriate instrumentation (see Example 14).

It is understood according to the practice of the invention that as long as plasma or extract thereof is provided that stabilizes the activity in a resultant control of factors II, V or VIII, selection of the donor mammal (whether primate or non-primate) for the remaining plasma components is generally without limitation as would be immediately apparent to those skilled in the art. Additionally, it is within the practice of the invention to readily determine other source mammals for stable factors II, V, and VIII, or those having high concentrations thereof.

EXAMPLE 14

Modification of Clotting Time For a Whole Blood Clotting Control into the Therapeutic Range The control of Example 13 was modified to provide a therapeutic clotting time as measured according to the ACTester (QUESTester) methodology (Kendall McGraw Company/Quest Medical, Dallas, Tex.). In order to adjust the clotting time to 200 seconds or more, dextran sulfate (15 mg/liter) was added thereto to provide a final concentration therein of 0.015 mg/liter. Suitable substitutes as are known in the art (such as heparin) may also be used.

EXAMPLE 15

Controls produced according to the practice of the invention have great stability as measured by their ability to confirm that the coagulation (clotting) time for a patient during a clinical program does not vary by more than about 10% from a predetermined value thereof. Such stability of controls (for example, reconstituted lyophilized controls) is evident even after storage under lyophilized conditions of up to 110 days at 37° C. or, for example, following more than 2, typically more than 5, and even up to 10 years at 2 to 8° C.

Representative of a lyophilization procedure useful in the production of such controls is lyophilization using 900 ml of blended plasma (⅓ each of beef, pig and horse) in combination with 100 ml of preservative solution comprising, for example, 0.2M Hepes pH 7.35, thimersol 0.2% and $NaN_3$ at 1% (see also the representative preservative solutions described above).

What is claimed is:

1. A stable whole blood coagulation control sample having a predetermined clotting time within the range of normal human clotting times for reproducibly monitoring coagulation capability in a human patient wherein said control sample comprises (1) mammalian whole blood which has been frozen and thawed and from which only cell membrane debris and platelet membrane ghosts are substantially removed to provide a whole blood supernatant, said mammalian whole blood supernatant comprising platelet membrane material, clotting factors, hemoglobin and platelet factor 3; and (2) an amount of at least one non-primate plasma or plasma extract that stabilizes or increases the activity of coagulation factor II, V and VIII.

2. A whole blood coagulation control sample according to claim 1 wherein said coagulation control comprises whole blood from a plurality of mammalian species, at least one of said mammalian species being a non-primate.

3. A whole blood coagulation control sample according to claim 1 further comprising buffer to maintain physiological pH and protease inhibitor.

4. A whole blood coagulation control sample according to claim 1 wherein said mammalian whole blood consists of non-primate mammalian blood.

5. A whole blood coagulation control sample according to claim 1 wherein said control sample is lyophilized.

6. A whole blood coagulation control sample according to claim 1 wherein said mammalian whole blood comprises primate blood or an extract therefrom, and further comprising swine plasma in an amount equal to at least about 1/5000 fraction of said primate blood.

7. A whole blood coagulation control sample according to claim 6 comprising primate blood plasma, or an extract therefrom, and further comprising a swine plasma in an amount equal to at least about a 1/1000 fraction of said primate blood plasma.

8. A whole blood coagulation control sample according to claim 6 comprising primate blood plasma, or an extract therefrom, and further comprising swine plasma in an amount equal to at least about a 1/100 fraction of said primate blood plasma.

9. A whole blood coagulation control sample according to claim 6 wherein said swine plasma therein provides an activity of factor VIII equal to at least about 50% of the activity of said factor VIII provided in said control sample by said primate blood.

10. A whole blood coagulation control sample according to claim 9 wherein said swine plasma therein provides an activity of factor VIII equal to at least about 70% of the activity of said factor VIII provided in said control sample by said primate blood.

11. A whole blood coagulation control sample according to claim 1 wherein said mammalian blood comprises primate blood plasma, or an extract therefrom, and further comprising bovine plasma in an amount equal to at least about a 1/5000 fraction of said primate blood plasma.

12. A whole blood coagulation control sample according to claim 11 comprising primate blood plasma, or an extract therefrom, and further comprising bovine plasma in an amount equal to at least about a 1/1000 fraction of said primate blood plasma.

13. A whole blood coagulation control sample according to claim 11 comprising primate blood plasma, or an extract therefrom, and further comprising bovine plasma in an amount equal to at least about a 1/100 fraction of said primate blood plasma.

14. A whole blood coagulation control sample according to claim 11 wherein said bovine plasma therein provides an activity of factor V equal to at least about 50% of the activity of said factor V provided in said control sample by said primate blood plasma.

15. A whole blood coagulation control sample according to claim 14 wherein said bovine plasma therein provides an activity of factor V equal to at least about 70% of the activity of said factor V provided in said control sample by said primate blood plasma.

16. A whole blood coagulation control sample according to claim 1 wherein said mammalian blood comprises primate blood plasma, or an extract therefrom, and further comprising horse plasma in an amount equal to at least about a 1/5000 fraction of said primate blood plasma.

17. A whole blood coagulation control sample according to claim 16 comprising primate blood plasma, or an extract therefrom, and further comprising horse plasma in an amount equal to at least about a 1/1000 fraction of said primate blood plasma.

18. A whole blood coagulation control sample according to claim 16 comprising primate blood plasma, or an extract therefrom, and further comprising horse plasma in an amount equal to at least about a 1/100 fraction of said volume of primate blood plasma.

19. A whole blood coagulation control sample according to claim 16 wherein said horse plasma therein provides an activity of factor II equal to at least about 50% of the activity of said factor II provided in said control sample by said primate blood plasma.

20. A whole blood coagulation control sample according to claim 19 wherein said horse plasma therein provides an activity of factor II equal to at least about 70% of the activity of said factor II provided in said control sample by said primate blood plasma.

21. A stable whole blood coagulation control sample having a predetermined clotting time within the range of abnormal human clotting times for reproducibly monitoring coagulation capability in a human patient wherein said control sample comprises (1) mammalian whole blood which has been frozen and thawed and from which only cell membrane debris and platelet membrane ghosts are substantially removed to provide a whole blood supernatant, said mammalian whole blood supernatant comprising platelet membrane material, clotting factors, hemoglobin and platelet factor 3;

wherein said mammalian whole blood supernatant is admixed with an effective amount of an agent that alters the clotting time of the mammalian whole blood; and (2) an amount of at least one non-primate plasma or plasma extract that stabilizes or increases the activity of coagulation factor II, V and VIII.

22. A whole blood coagulation control sample according to claim 21 wherein said mammalian blood is non-primate mammalian blood.

23. A whole blood coagulation control sample according to claim 21 wherein said agent is heparin or dextran sulfate.

24. A whole blood coagulation control sample according to claim 21 wherein the agent is present in an amount of 0.015 mg/liter.

* * * * *